United States Patent [19]

Treiber et al.

[11] Patent Number: 5,192,668
[45] Date of Patent: Mar. 9, 1993

[54] SYNTHESIS OF PROTEASE INHIBITOR

[75] Inventors: Laszlo R. Treiber, Gillette; Lawrence F. Colwell, Jr., Eatontown; Byron H. Arison, Watchung; Georgette Dezeny, Short Hills; Russell B. Lingham, Watchung, all of N.J.; Wayne J. Thompson, Lansdale; Suresh K. Balani, Hatfield, both of Pa.

[73] Assignee: Merck & Co., Inc., Rahway, N.J.

[21] Appl. No.: 842,814

[22] Filed: Feb. 27, 1992

Related U.S. Application Data

[63] Continuation of Ser. No. 595,895, Oct. 11, 1990, abandoned.

[51] Int. Cl.$^5$ ............................ C12P 1/00; C12P 21/04
[52] U.S. Cl. ...................................... 435/41; 435/71.1; 435/120; 435/253.5; 544/60
[58] Field of Search .................. 435/253.5, 41, 71.1, 435/120; 544/60

[56] References Cited

U.S. PATENT DOCUMENTS

| | | | |
|---|---|---|---|
| 4,661,473 | 4/1987 | Boger et al. | 514/16 |
| 4,965,200 | 10/1990 | Chen et al. | 435/125 |
| 4,980,283 | 12/1990 | Huang et al. | 435/71.2 |
| 4,996,149 | 2/1991 | Jarreau et al. | 435/119 |

OTHER PUBLICATIONS

Ser. No. 07/452,912 filed Dec. 18, 1989 Merck Case 18025.
Ser. No. 07/595,905 filed Oct. 10, 1990 by Treiber (Merck 18166).
Ser. No. 07/595,909 filed Oct. 11, 1990 by Balani (Merck 18207).
Ser. No. 07/595,894 filed Oct. 11, 1990 by Chen (Merck 18208).
Power, M. D. et al., "Nucleotide Sequence of SRV-1 . . .," Science 231, 1567 (1986).
Pearl, L. H. et al., "A structural model for retroviral proteases," Nature 329, 351 (1987).
Evans, B. E. et al., "A Stereocontrolled Synthesis . . . ," J. Org. Chem. 50, 4615 (1985) (Evans I).
Crawford, S. et al., "A Deletion Mutant in . . . pol . . . Blocks Proteolytic Processing . . . ," J. Virol. 53, 899 (1985).
Ratner, L. et al., "Complete Nucleotide Sequence in AIDS Virus, HTLV-III," Nature 313, 277 (1985).
Toh, H. et al., "Close Structural Resemblance . . . ," EMBO J 4, 1267 (1985).
Evans, B. E. et al., "A Stereocontrolled Synthesis . . . ," Proc. Am. Pept. Symp., 9, 743 (1985) (Evans II).
Luly, J. R. et al., "A Synthesis of Protected Aminoalkyl Epoxides," J. Org. Chem. 52, 1487 (1987).
ASM News, vol. 56, No. 7, (Jul. 1990) at 368.

*Primary Examiner*—Merrell C. Cashion, Jr.
*Assistant Examiner*—Bennett Celsa
*Attorney, Agent, or Firm*—Roy D. Meredith; Charles M. Caruso

[57] ABSTRACT

A dipeptide isostere is the biotransformed product after incubation with a culture of Streptomyces. It inhibits HIV protease, and is useful in the prevention or treatment of infection by HIV and the treatment of AIDS, either as a compound, pharmaceutically acceptable salt, pharmaceutical composition ingredient, whether or not as a prodrug or as a combination with other antivirals, anti-infectives, immunomodulators, antibiotics or vaccines. Methods of treating AIDS and methods of preventing or treating infection by HIV are also described.

1 Claim, No Drawings

SYNTHESIS OF PROTEASE INHIBITOR

This is a continuation of application Ser. No. 07/595,895, filed Oct. 11, 1990 now abandoned This application is related to Ser. No. 07/619,654 filed on Dec. 4, 1990 which is a continuation-in-part of Ser. No. 07/597,286 filed on Oct. 15, 1990 which is a file wrapper continuation of parent case Ser. No. 07/452,912, filed on Dec. 18, 1989, all abandoned.

The present invention is concerned with a compound which inhibits the protease encoded by human immunodeficiency virus (HIV). The compound, or pharmaceutically acceptable salt thereof, is of value in the prevention of infection by HIV, the treatment of infection by HIV and the treatment of the resulting acquired immune deficiency syndrome (AIDS). The present invention also relates to pharmaceutical compositions containing the compound and to a method of use of the present compound with or without other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Interruption of this processing appears to prevent the production of normally infectious virus. For example, Crawford, S. et al., J. Virol., 53, 899 (1985) demonstrated that genetic deletion mutations of the protease in murine leukemia virus which prevent processing of precursor structural proteins result in non-infectious viral particles. Unprocessed structural proteins also have been observed in clones of non-infectious HIV strains isolated from human patients. These results suggest that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

Applicants demonstrate that the compound of this invention is an inhibitor of HIV protease.

BRIEF DESCRIPTION OF THE INVENTION

A biotransformed compound, as herein defined, is disclosed. This compound is useful in the inhibition of HIV protease, the prevention of infection by HIV, the treatment of infection by HIV and in the treatment of AIDS and/or ARC, either as a compound, pharmaceutically acceptable salt (when appropriate), pharmaceutical composition ingredient, whether or not as a prodrug or as a combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with the use of a compound of the structure given below or pharmaceutically acceptable salt thereof, in the inhibition of HIV protease, the prevention or treatment of infection by HIV and in the treatment of the resulting acquired immune deficiency syndrome (AIDS). The biotransformed compound is produced by the cultivation of Streptomyces culture ATCC 55095 with L-689,502, an HIV protease inhibitor. The biotransformed compound was found to have the structure:

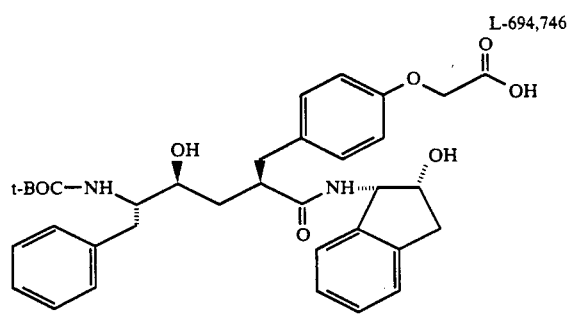

L-694,746

, or pharmaceutically acceptable salt thereof.

The pharmaceutically-acceptable salts of the compound of the present invention (in the form of water- or oil-soluble or dispersible products) include the conventional non-toxic salts or the quaternary ammonium salts of this compound, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Hydrates, esters or amides are also encompassed by the present invention. Such hydrates, esters or amides are those which would readily occur to the skilled artisan, and include, for example, $C_{1-4}$ alkyl esters and amides.

The compound of the present invention is useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compound of this invention is useful in treating infection by HIV after suspected past exposure to HIV by e.g., blood transfusion, accidental needle stick, or exposure to patient blood during surgery.

For these purposes, the compound of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of the compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the HIV protease inhibitor compound with one or more agents useful in the treatment of AIDS. For example, the compound of this invention may be effectively administered, whether at periods of pre-exposure and/or post-exposure, in combination with effective amounts of other AIDS antivirals, immunomodulators, anti-infectives, or vaccines.

BIOTRANSFORMATION OF PARENT COMPOUND L-689.502

The novel antibacterial compound of the present invention is produced during the aerobic fermentation of suitable aqueous nutrient media under controlled conditions via inoculation with the organism Streptomyces culture #S-26-487 (ATCC 55095), also designated MA-6804. Aqueous media, such as those employed for the production of antibiotics are suitable for producing the novel compound of the present invention. Such media contain sources of carbon, nitrogen and inorganic salts assimilable by the microorganism. Many fermentation media support biotransformation of L-689,502 into L-694,746 by Streptomyces culture #S-26-487, and may be suitably adjusted within the routine skill of the fermentation microbiologist.

In general, carbohydrates, for example, glucose, fructose or starches as well as glycerol, pectin or peptonized milk either alone or in combination can be used as sources of assimilable carbon in the nutrient medium. The exact quantity of the carbon source or sources utilized in the medium depends in part upon the other ingredients of the medium but, in general, the amount of carbon source usually varies between about 1% and 6% by weight of the medium. These carbon sources can be used individually or several such carbon sources can be combined in the medium.

Many proteinaceous materials may be used as nitrogen sources in the fermentation process. Suitable nitrogen sources include, for example, yeast extract, yeast hydrolysates, soybean flour, distillers solubles, corn steep, peptonized milk, lard water, peanut meal and tomato paste and the like. The sources of nitrogen, either alone or in combination, are used in amounts ranging from about 0.2% to 6% by weight of the aqueous medium.

Among the nutrient inorganic salts which may be incorporated in the medium are the customary salts capable of yielding sodium, potassium, ammonium, calcium, magnesium, phosphate, sulfate, chloride, carbonate and the like ions. Also, there may be included trace metals such as cobalt, manganese and iron.

The fermentation is typically carried out in a baffled flask at temperatures ranging from about 20° C. to about 42° C., preferably about 27° C. The pH of the nutrient media suitable for growing Streptomyces culture #S-26-487 and producing the novel compound of the present invention should be in the range of from about 5.5 to 8.0, preferably about 7.0.

Small scale fermentation of the antibiotic conveniently is carried out by inoculating a suitable nutrient medium with the culture and, after transfer to a production medium, permitting fermentation under aerobic conditions to proceed at a constant temperature on a shaker for several days. At the end of the incubation period, the biotransformed product is isolated from the fermentation broth by techniques hereinafter described.

The small scale fermentation may be conducted in a sterilized flask via a one, two, three or four-stage seed development. The nutrient medium for the seed stage may be any suitable combination of carbon and nitrogen sources. The seed flask is shaken in a constant temperature chamber until maximum growth is completed (usually 1-3 days) and some of the resulting growth is used to inoculate either a further seed-stage or the production medium. Intermediate stage seed-flasks, when used, are developed essentially in the same manner; that is, part of the contents of the flask is used to inoculate either the next stage seed medium or the production medium. The inoculated production flasks are shaken at a constant temperature for several days (usually 3 to 5 days) and at the end of the incubation period the novel compound of the present invention is isolated.

For large scale work, it is preferable to conduct the fermentation in suitable tanks provided with an agitator and a means of maintaining the fermentation medium under aerobic conditions. The nutrient medium is made up in the tank and sterilized by heating to about 120° C. Upon cooling, the sterilized medium is inoculated with a previously grown seed culture of the producing organism and fermentation is permitted to proceed for a period of several days (3 to 5 days, for example) while maintaining a constant temperature.

It will be understood that, given the guidelines and experimental protocols of this application, the determination of appropriate fermenting or culturing conditions for Streptomyces #S-26-487, is well within the scope of this invention. Such conditions, including small and large scale fermentation, are conventional adaptations or common variations easily ascertained by one with the requisite skills.

Characteristics of the Biotransforming Microorganism MA-6804

Analysis of Cell Wall Composition

MA-6804 peptidoglycan contains L-diaminopimelic acid. Whole cell sugar analysis reveals galactose, mannose, madurose, and traces of glucose.

General growth characteristics

MA-6804 strain grows well on yeast malt extract, glycerol asparagine, inorganic salts-starch, oatmeal, and trypticase soy agars. Growth occurs at 27° and 37° C. The culture also grows well in liquid media such as yeast dextrose broth.

Colony morphology (on yeast malt extract agar)

MA-6804: Substrate mycelium is medium yellow (89 m. Y) and colonies are opaque, raised, lobate and rubbery. The colony surface is rough. Aerial mycelia appear after 2 days incubation and are white in color (263 White). Spore mass, when present, is light brown gray (63 l. br. Gy).

Micromorphology

MA-6804 aerial mycelia (0.57 μm dia.) radiate from the substrate mycelium and are straight. In mature cultures, aerial mycelia terminate in chains of spores that are borne in flexuous chains or wide loops.

Miscellaneous physiological reactions

MA-6804 culture produces melanoid pigments in tryptone yeast extract broth, yeast extract broth, and peptone yeast extract iron agar in 2-3 d. Starch is not hydrolyzed. Carbon source utilization pattern is as follows: D-raffinose; moderate utilization of cellobiose, D-maltose, D-mannose; poor utilization of D-fructose; no utilization of D-arabinose, L-arabinose, inositol, α-D-lactose, β-D-lactose, D-mannitol, L-rhamnose, sucrose, D-xylose, L-xylose.

Diagnosis

The chemotaxonomic and morphological characteristics of this strain compare favorably with the published description of members of the genus Streptomyces. There are some similarities to the carbon utilization pattern of *Streptomyces pactum*. However, *S. pactum* does not produce melanoid pigments and has colorless vegetative growth. Among the red series, MA-6804 bears strong similarities to *Streptomyces xanthophaeus* (which is currently considered a subjective synonym of *S. lavendulae*, Bergey's Manual of Systematic Bacteriology, Volume 4, 1989). Some strains of this species are reported to be gray in color. The coloration of the vegetative mycelium and the production of melanoid pigments is also consistent with *Streptomyces lavendulae*. MA-6804 is tentatively identified as a strain of *Streptomyces lavendulae*.

ATCC DEPOSITS

On or about Sep. 19, 1990, a sample of MA-6804, also designated S-26-487, was deposited at the American Type Culture Collection (ATCC), 12301 Parklawn Drive, Rockville MD 20852. The culture access designation is 55095. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

EXAMPLE 1

Synthesis Of Patent Compound L-689,502

The preparation and synthesis follows, in general, U.S. Pat. No. 4,661,473; Evans, B.E. et al, *J. Org. Chem.*, 50, 4615, (1985) and Evans, B.E. et al., "A Stereocontrolled Synthesis of Hydroxyethylene Dipeptide Isosteres," Proc. Am. Pept. Symp., 9, 743–6 (1985), and Luly, J.R. et al, J. Org. Chem, 52, 1487 (1987), all herein incorporated by reference. All temperatures are in degrees centigrade, unless indicated otherwise.

Preparation of N-(cis-2(R)-hydroxy-1(S)-indanyl)-5(S)-(1,1-dimethylethoxycarbonylamino)-4(S)-hydroxy-6-phenyl-2(R)-[(4-(2-(4-morpholinyl)ethoxy)phenyl)methyl]-hexanamide, L-689,502

Step A: Preparation of N-3(S)-[(1,1-Dimethylethoxycarbonyl)amino]-2(RS)-hydroxy-4-phenyl-1-trimethylsilyl butane To a stirred suspension of magnesium turnings (9.79 g, 403 mmol) in dry diethyl ether (200 mL) under nitrogen was added chloromethyltrimethylsilane (50 mL, 358 mmol). The reaction was initiated by gentle warming and then was cooled in an ice bath to maintain gentle reflux. After exotherm was complete the reaction was stirred at room temperature for 1 hour then cooled to −78° C. in a dry ice/acetone bath. To the solution of the Grignard was added dropwise with stirring a solution of N-2(S)-[(1,1-dimethylethoxycarbonyl)amino]-3-phenyl propionaldehyde (19.3 g, 77.4 mmol) in dry diethyl ether (250 mL) dropwise such that the temperature of the reaction remained below −55° C. The resultant gray suspension was allowed to warm to room temperature where it was stirred for 30 minutes then was quenched by pouring into a mixture of ice (500 g) and 10% citric acid (500 mL). The organic phase was collected and the aqueous phase was extracted with diethyl ether (3×300 mL). The combined organics were washed with 10% citric acid (1×300 mL) and brine (1×200 mL), dried over anhydrous magnesium sulfate, filtered, and concentrated to give crude N-3(S)-[(1,1-dimethylethoxycarbonyl)amino]-2(RS)-hydroxy-4-phenyl-1-trimethylsilyl butane (26.6 g, quantitative crude yield) as a yellow oil. An analytical sample was obtained by low pressure chromatography (silica gel, 230–400 mesh; diethyl ether: hexanes, 30%:70%) followed by recrystallization from heptane. mp=91°–95° C.; elemental analysis. Calcd. for $C_{18}H_{31}NO_3Si$ (337.53): C=64.05, H=9.26, N=4.15; Found: C=64.05, H=9.13, N=4.22; $[a]_D^{20}$=−40.0°.

Step B: Preparation of 3(S)-Amino-4-phenyl-1-butene

To a stirred solution of the product of Step A (22.8 g, 67.5 mmoL) in dry methylene chloride (400 mL) cooled in an ice bath and under nitrogen was added in a fine stream boron trifluoride etherate (43 mL, 345 mmol). The solution was allowed to warm to room temperature where it was stirred for 4 days. Reaction was cooled in an ice bath and quenched by the dropwise addition of 10% sodium hydroxide (400 mL). The organic phase was collected and the aqueous phase was extracted with methylene chloride (2×250 mL). The combined organics were washed with brine (1×200 mL), dried over anhydrous magnesium sulfate, filtered, and concentrated to give crude 3(S)-amino-4-phenyl-1-butene (14.2 g) as a yellow oil.

Step C: Preparation of N-3(S)-[(1,1-Dimethylethoxycarbonyl)amino]-4-phenyl-1-butene A solution of the product of Step B (14.2 g) and di-tert-butyl dicarbonate (31.0 g, 142 mmoL) in dry methylene chloride (200 mL) was stirred at room temperature for 18 hours, washed with 10% citric acid (3×100 mL), water (1×100 mL), sat'd. sodium bicarbonate (3×125 mL), and brine (1×250 mL), dried over anhydrous magnesium sulfate, filtered and concentrated to yield crude N-3(S)-1[(1,1-dimethylethoxycarbonyl)amino]-4-phenylbutene (34.6 g) as a yellow oil. Crude product was purified by low pressure chromatography (silica gel, 230–400 mesh, 10×20 cm column; diethylether: hexanes, 20% 80%) to yield N-3(S)-[(1,1-dimethylethoxylcarbonyl)amino]-4-phenyl-1-butene (16.3 g, 97.6% yield) as a white solid. An analytical sample was obtained by recrystallization from heptane. mp=67.5°–68.5° C.; elemental analysis, Calcd. for $C_{15}H_{21}NO_2$ (247.34): C=72.84, H=8.56, N=5.66. Found: C=72.78, H=8.76, N=5.64.

Step D: Preparation of 1(R)-[1'(S)-(1,1-Dimethylethoxycarbonyl)amino-2-phenylethyl]oxirane To a solution of the product of Step C (9.4 g, 38 mmol) in dry methylene chloride (100 mL) cooled in an ice bath and under nitrogen was added 3-chloroperoxybenzoic acid (technical grade, 80–85%; 41 g, 200 mmol). The mixture was stirred at 0° C. for 18 hours and 25° C. for 23 hours, then diluted with diethyl ether (300 mL), and poured in ice cold aqeous 10% sodium sulfite (1 L). The organic layer was collected and the aqueous layer was extracted with diethyl ether (3×100 mL). The combined organics were washed with 10% sodium sulfite (3×100 mL), satd. sodium bicarbonate (3×100 mL), and brine (1×100 mL), dried over anhydrous sodium sulfate, filtered and concentrated to give a white solid. Crude product was purified by low pressure chromatography (silica gel 230–400 mesh, 8×15 cm column; ethyl acetate:hexanes, 25%:75%) to yield 1(R)-[1'(S)-(1,1-dimethylethoxycarbonyl)amino-2-phenylethyl]oxirane (7.0 g, 70% yield) as a clear oil which crystallized upon standing. An analytical sample was obtained by recrystallization from heptane. mp=51.5°–52° C.; elemental analysis, Calcd. for $C_{15}H_{21}NO_2$ (263.34): C=68.42, H=8.04, N=5.32. Found: C=68.22, H=8.26, N=5.29; $[a]_D^{20}$=1.34°.

Step E: Preparation of (5S,1'S)-3-carboethoxy-5-(1-((1',1'-dimethylethoxycarbonyl)amino)-2-phenylethyl)-dihydrofuran-2-(3H)-one.

The product from Step D, 9.93 g, was dissolved in 100 mL of absolute ethanol and added to a solution of 2.6 g of sodium and 20.1 mL of diethyl malonate in 170 mL of absolute ethanol. After stirring overnite, the reaction was acidified to pH 4 with 10% citric acid and extracted with 2×500 mL of ether. The combined organic extracts were washed 1×500 mL $H_2O$, 1×500 mL sat'd $NaHCO_3$, 1×500 mL sat'd brine and dried over $MgSO_4$. The solvents were removed and the crude product purified by low pressure chromatography on silica gel eluting with 50% ether/hexanes (or EtOAc/hexanes). The yield of semi-solid product was 10.6 g. The later fractions contained 2.5 g of the undesired 5 R isomer as a white solid.

Step F: Preparation of (5S,1'S)-3-carboethoxy-3-(4-benzyloxyphenylmethyl)-5-[1-(1,1-dimethylethoxycarbonyl)amino)-2-phenylethyl]dihydrofuran-2-(3H)-one To a stirred solution of (5S,1'S)-3-carboethoxy-5-[1-((1',1'-dimethylethoxycarbonyl)amino)-7-phenylethyl]-dihydrofuran-2-(3H)-one (product of Step E), 2 g (5.3 mmol) in 25 mL of absolute ethanol was added a solution of 0.13 g of sodium in 2.2 mL of absolute ethanol followed by 1.30 g (5.5 mmol) of 4-benzyloxybenzyl chloride. The solution was heated to 50° C. under nitrogen for 1 hour, then cooled in an ice bath and acidified with 20 mL of 10% citric acid and diluted with 200 mL of water. The mixture was extracted with 3×100 mL of ether and the combined ether extracts washed with 50 mL of water, 200 mL of sat'd $NaHCO_3$ and dried over $MgSO_4$. Removal of solvents under reduced pressure and purification by low pressure chromatography on silica gel, eluting with 40% ether in hexanes gave 1.56 g (51% yield) of a clear colorless glass essentially homogeneous by TLC (50% ether/hexanes).

Step G: Preparation of (3R,5S,1')-3-(4-benzyloxyphenylmethyl)-5-(1((1,1-dimethylethoxycarbonyl)amino)-2-phenylethyl)-dihydrofuran-2-(3H)-one The product of Step F, 13.6 g, was dissolved in 250 mL of 1,2-dimethoxyethane, and to it was added 117 mL of 1M lithium hydroxide at room temperature. After stirring for 12 hours, the solvents were removed under reduced pressure, the residue suspended in 200 mL of 10% citric acid and extracted 3×500 mL of diethyl ether. The combined ether extracts were washed with 500 mL of brine, dried (MgSO$_4$) and the concentrated to dryness. The residue was dissolved in 250 mL of toluene, heated to reflux for 12 hours, then concentrated to dryness under reduced pressure. Purification by medium pressure chromatography over silica gel eluting with 15% ethyl acetate/hexanes gave 3.2 g of the 3R-lactone as a clear foam. Further elution with the same solvents gave 6.15 g of the 3S-lactone as a white solid.

Step H: Preparation of N'-(1,1-dimethylethoxycarbonyl)-5(S)-amino-4(S)-(1',1'-dimethylethyl-1,1-dimethylsilyloxy)-6-phenyl-2(R)-(4-benzyloxyphenylmethyl-hexanoic acid.

The product of Step G, 0.6 g, was dissolved in 30 mL of a 2:1 mixture of ethylene glycol dimethyl ether/water, and to it was added 5 mL of 1M lithium hydroxide at room temperature. After stirring for 1 hour, the mixture was partitioned between 200 mL chloroform and 20 mL 10% citric acid. The layers were separated and the aqueous phase extracted with 3 ×20 mL chloroform. The combined organic layers were dried (Na$_2$SO$_4$) and the solvent removed to yield 0.56 g of the crude hydroxy acid. This residue was dissolved in 5 mL of dry DMF and 0.845 g tert-butyl dimethylsilyl chloride and 0.725 g of imidazole were added. After stirring for 18 hours, the reaction was poured into 50 mL of water and extracted with 3×20 mL of ethyl acetate. The combined organic extracts were washed with 3×20 mL of 10% citric acid, 1×20 mL of water, 3×10 mL of saturated aqueous solution of Na$_2$CO$_3$, and 20 mL of brine. After drying (Na$_2$SO$_4$), the solvent was removed and the resulting residue dissolved in a mixture of 5 mL of THF, 5 mL of glacial acetic acid, and 2 mL of water. The mixture was stirred for 4 hours, then poured into 50 mL of water and extracted with 3×20 mL of ether. The combined ether extracts were washed with 2×20 mL of water, brine, dried (Na$_2$SO$_4$), and the solvent removed. Purification by medium pressure chromatography over silica gel, eluting with MeOH/CHCl$_3$ gave 0.60 g of the product as a white glassy solid.

Step I: Resolution of 1-Amino-2-hydroxyindan

From the known racemic 1-amino-2-hydroxyindan, the resolution was carried out as described for the 3-amino-1,2-dihydroxyindan in Example 7 below (Steps D and E). The (1S,2R)-1-amino-2-hydroxyindan resulting from saponification of the higher R$_f$ diastereomer was shown to have an a$_D$ of −58° (c=1.0, CHCl$_3$). The (1R, 2S)-1-amino-2-hydroxyindan resulting from saponification of the lower R$_f$ diastereomer was found to have an a$_D$ of +62° (c=1.0, CHCl$_3$).

Step J: Preparation of N-(2(R)-hydroxy-1(S)-indanyl)-5(S)-(1,1-dimethylethoxycarbonylamino)-4(S)hydroxy-6-phenyl-2(R)-(4-benzyloxyphenylmethyl) hexanamide The product from Step H, 0.12 g, was dissolved in 2 ml dry DMF and to it was added 40 mg of 1(S)-amino-2(R)-hydroxyindane, (Step I) 25 mg of 1-hydroxybenzotriazole hydrate and 70 mg of dimethyl-3-(3-dimethyl aminopropyl)carbodiimide hydrochloride. Triethylamine was added to the stirred solution until the pH was 8.5 (32 mL). After stirring for concentrated to dryness under reduced pressure, the residue was dissolved in 100 mL of chloroform and worked with 1×50 mL of 10% citric acid, 1×50 mL H$_2$O, 1×50 mL sat'd NaHCO$_3$, dried over MgSO$_4$ and concentrated to dryness. The residue was dissolved in 1 mL of tetrahydrofuran and added to 2 mL of 1M tetrabutylammonium fluoride in THF. After stirring overnight at room temperature the reaction mixture was diluted with 10 mL of 10% citric acid and the white precipitate collected by filtration. The product was purified by low pressure chromatography on silica gel eluting with 2% methanol/CH$_2$Cl$_2$ to give 85 mg of product which was essentially homogeneous by TLC (3% methanol/CH$_2$Cl$_2$).

Step K: Preparation of N-(2(R)-hydroxy-1(S)-indanyl)-5(S)-(1,1-dimethylethoxycarbonylamino)-4(S)hydroxy-6-phenyl-2(R)-(4-hydroxyphenylmethyl)hexanamide The product of Step J, 85 mg was dissolved in 10 mL of methanol and 10 mL of THF, and to it was added 0.10 g of 10% palladium on carbon. The mixture was stirred under an atmosphere of hydrogen for 48 hours at room temperature, then filtered and concentrated to dryness. The residue was dissolved in 10 mL of hot ethanol and 20 mL water was added. On cooling the white solid precipitate was collected and dried under vacuum over P$_2$O$_5$. The yield was 72 mg (98% yield) of pure product: mp 218°–219° C. (effervesces, sinters at 215) elemental analysis, Calc'd for C$_{33}$H$_{40}$N$_2$O$_6$: (560.696): C, 70.69; H, 7.19; N, 5.00; Found: C, 70.62; H, 7.39; N, 4.79.

Step L: Preparation of N-(cis-2(R)-hydroxy-1(S)-indanyl)-5(S)-[1,1-dimethylethoxycarbonylamino)-4(S)-hydroxy-6-phenyl-2(R)[(4-(2-(4-morpholinyl)ethoxy)phenyl]methyl]hexanamide A stirred mixture of Step K product, N-(2(R)hydroxy-1(S)-indanyl)-5(S)-[1,1-dimethylethoxycarbonyl)amino]-4(S)-hydroxy-6-phenyl-2(R)-(4-hydroxyphenylmethyl) hexanamide (0.50 g, 0.9 mmol), anhydrous cesium carbonate (1.0 g, 3 mmol) and N-(2-chloroethyl) morpholine, free base (2.35 g, 17 mmole) in 100 mL of anhydrous dioxane was heated to 80° C. (internal temperature) for 3 hrs. After cooling to room temperature the mixture was diluted with chloroform (50 mL) filtered, concentrated to dryness under reduced pressure, and the residue triturated with 50 ml of anhydrous ether and 10 mL of ethyl acetate. The white solid product was collected and dried under vacuum over P$_2$O$_5$. The yield was 0.54 g (89%) of pure product: mp 195°–7° C. elemental analysis, Calc'd. for C$_3$H$_{51}$N$_3$O: (673.856): C, 69.52 H, 7.63; N, 6.23; Found: C, 69.19 H, 7.45; N, 6.15.

maleate hydrate:

mp 112°–113° C. dec. elemental analysis, Calc'd. for C$_{39}$H$_{51}$N$_3$O$_7$.C$_4$H$_4$O$_4$.H$_2$O: (807.946): C, 63.92 H, 7.11; N, 5.20; Found: C, 64.23 H, 6.94; N, 5.10.

EXAMPLE 2

Biotransformation of L-689,502

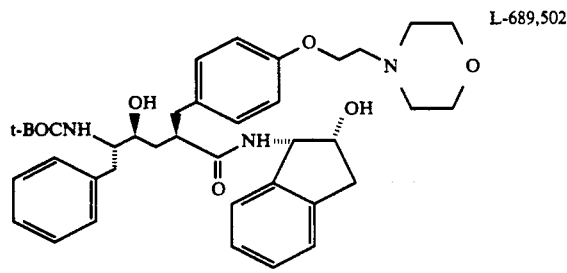

L-689,502

A frozen vial (2.5 ml) of Streptomyces culture #S-26-487 was used to inoculate the fermentation medium (50 ml) in a 250 ml baffled Erlenmeyer flask. After 48 hours of incubation at 27° C. and 220 RPM, the seed (2.5 ml) was transferred to 250 ml baffled Erlenmeyer flasks containing new fermentation medium (50 ml each). The conditions of cultivation were the same as in the seed stage. After 48 hours of incubation, the substrate (L-689,502, 2.2 mg in 1 ml DMSO per flask) was added to the flasks and the incubation continued under the same conditions for 72 hours to yield L-694,746 as the main product.

Fermentation medium:

| Ingredient | Conc. (g/l) |
| --- | --- |
| Dextrose | 4.0 |
| Malt Extract | 10.0 |
| Yeast Extract | 4.0 |
| Nutrient Broth | 4.0 |
| pH adjusted to 7.0 | |

EXAMPLE 3

Isolation and Purification of Biotransformed Metabolites

HPLC methods were used for the isolation work and for monitoring the fermentation and purification steps. The preparative runs were monitored at 225 nm. The analytical runs were monitored at 215 and 225 nm, and the spectrum of each peak was stored in the computer file. C$_{18}$ chromatographic medium was used for both the analytical (4.6 mm×25 cm) and the preparative (10 mm×25 cm) separations. The flow rates were 0.9 ml/min. and 3.0 ml/min, respectively. In two different gradient methods, two electrolyte solutions (solvent A) were used as aqueous component. The neutral buffer (pH 6.2) was 20 mM ammonium phosphate solution. The acidic solution was 10 mM phosphoric acid. The organic phase (solvent B) was acetonitrile-water (85:15 v/v).

One biotransformation batch for preparative isolation consisted of nine shakeflask samples. The corresponding samples were combined. Sodium sulfate was added to the whole broths to ca. 5% concentration. The whole broths were extracted with methyl ethyl ketone (MEK) twice, one volume each time. The pooled MEK extracts were evaporated in vacuo to an oil. The residue was sonicated with methanol (5 ml) and centrifuged to separate the precipitate formed. The supernatant was evaporated to dryness and redissolved in methanol (1 ml) for preparative HPLC separation. The first separations were performed in the neutral gradient. The corresponding fractions from multiple runs were combined and evaporated to dryness. The final purification of the fractions was completed in the acidic gradient. The fractions were collected according to the peaks detected. In the areas not showing any significant peak, 2 minute fractions were collected. The fractions containing the pure products were combined, neutralized with conc. NH$_4$OH and evaporated to dryness. The product was separated by selectively dissolving it with methanol from the insoluble ammonium phosphate.

The gradient programs were as follows:

| | Time (min) | Solvent B % |
| --- | --- | --- |
| Analytical, neutral: | 0–2 | 35 |
| | 2–3 | 35–45 |
| | 3–10 | 45–65 |
| | 10–12 | 65–100 |
| | 12–17 | 100 |
| | 17–18 | 100–35 |
| Analytical, acidic: | 0–2 | 30 |
| | 2–18 | 30–80 |
| | 18–20 | 80–100 |
| | 20–24 | 100 |
| | 24–25 | 100–30 |
| Preparative, neutral: | 0–2.5 | 35 |
| | 2.5–7 | 35–45 |
| | 7–30 | 45–65 |
| | 30–34.5 | 65–100 |
| | 34.5–43 | 100 |
| | 43–44 | 100–35 |
| Preparative, acidic: | 0–2.5 | 30 |
| | 2.5–30 | 30–75 |
| | 30–32 | 75–100 |
| | 32–43 | 100 |
| | 43–44 | 100–30 |

L-694,746: The extraction and chromatographic purification were performed as described above. In the neutral preparative HPLC, the peak eluting at 13.4 min was collected. This fraction was then rechromatographed in the acidic preparative HPLC to give the final product at 25.4 min. After the isolation process, pure product was obtained. Physical losses account for the low overall recovery. The chemical structure was established by NMR and by MS studies.

Retention times (minutes):

| Compound | Neutral gradient | | Acidic gradient | |
| --- | --- | --- | --- | --- |
| | Anal. | Prep. | Anal. | Prep. |
| L-694,746 | 8.3 | 13.4 | 17.8 | 25.4 |
| L-689,502 | 14.6 | 31.6 | 15.2 | n.a. |

The structure of L-694,746 was determined to be as follows:

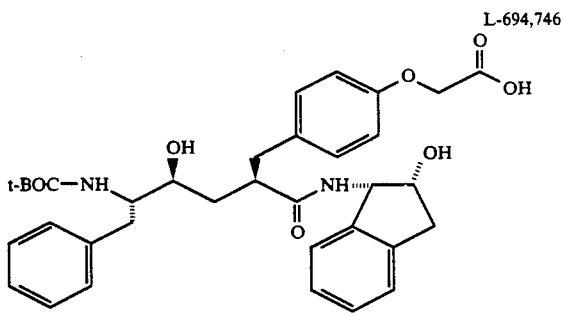

Key spectroscopic features by NMR were the absence of the morpholinoethyl signals and the presence of a two proton singlet at 4.65 ppm. Otherwise the NMR spectrum closely resembles parent L-689,502. Mass spectral analysis confirmed the structure under positive FAB-MS conditions using "magic bullet" (5:1 dithiothreitol/dithioerythritol) as the matrix.

EXAMPLE 4

Assay for Inhibition of Recombinant HIV Protease (APRIN 2.1)

Inhibition studies were performed on the reaction of the HIV protease expressed in Escherichia coli with a tritiated peptide substrate, [$^3$H]-acetyl-Val-Ser-Gln-Asn-(beta-napthyl-Ala)-Pro-Ile-Val-Gln-Gly-Arg-Arg-NH$_2$(MW 1800). The two arginine residues at the carboxyl terminus give this peptide an overall positive charge at acidic pH and enable it to bind to the H$^+$ form of DOWEX AG-50W-X8 resin and similar resins. The HIV protease cleaves between the β-napthyl-Ala and proline residues to yield a product ($^3$H-acetyl-val-ser-asn-(β-napthyl-ala) that is either neutral or slightly negatively charged and does not bind to the cation exchange resin. It is therefore possible to conveniently separate the labelled product from the substrate.

Aliquots of 25 μl containing 6.0–8.0 nM HIV protease in assay buffer (100 mM sodium acetate, pH 5.5 and 0.1% BSA) are placed in assay tubes. The reaction is initiated by addition of 25 μl aliquots of 4.2 μM tritiated peptide substrate in 100 mM sodium acetate, pH 5.5. After incubation for 60 min at 37° C., the reaction is stopped with 100 μl of 5% H$_3$PO$_4$, then analysed by application of column chromatography.

Results are as follows:

| (1) Control: APRIN 2.1 Activity of L-689,502: | |
|---|---|
| Conc. (ng/ml) | Inhibition (%) |
| 10 | 86 |
| 5 | 69 |
| 2.5 | 54 |
| 1.25 | 21 |
| 0.625 | −2 |

| (2) APRIN 2.1 Activity of Major Metabolites: | | | | |
|---|---|---|---|---|
| Culture # (Compound) | Retention Time (min) Prep. HPLC | Anal. HPLC | Conc. (ng/ml) | APRIN 2.1 Act. (% Inhib.) |
| L-694,746 | 13.45 | 8.38 | 1 | 88 |

EXAMPLE 5

Organic Synthesis of L-694,746

Nine grams of the product of Step K of Example 1, N-(2(R)-hydroxy-1(S)-indanyl)-5(S)-[1,1-dimethylethoxycarbonyl)amino]-4(S)-hydroxy-6-phenyl-2(R)-(4-hydroxyphenylmethyl) hexaneamide, was reacted with excess BrCH$_2$COOEt (9 mL), and anhydrous cesium carbonate (2 g) in 140 mL anhydrous dioxane. The mixture was heated to 80° C. for 24 hours, then cooled, filtered, concentrated and dried to yield the ethyl ester L-694,746 as a white solid. The ester was dissolved in 200 mL of THF and 7 mL of 1N LiOH was added. After 2 hours stirring, the mixture was diluted with methanol, acidified by stirring with Amberlite ® 120 ion exchange resin, filtered and concentrated to dryness. Trituration with diethyl ether and hexanes gave L-694,746 as the hydrate.

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A method of preparing a compound of the formula:

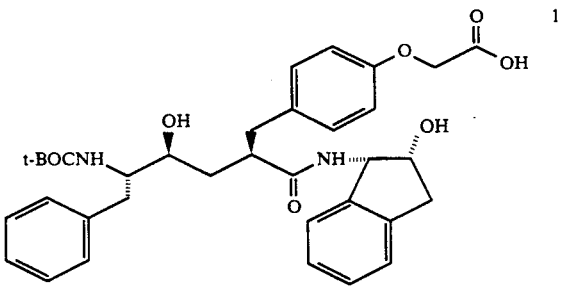

comprising the steps of
(1) providing a quantity of N-(Cis-2(R)-hydroxy-1(S)-indanyl)-5(S)-(1,1-dimethylethoxycarbonylamino)-4(S)-hydroxy-6-phenyl-2(R)-((4-(2-(4-morpholinyl)ethoxy)phenyl)methyl)-hexanamide of the formula:

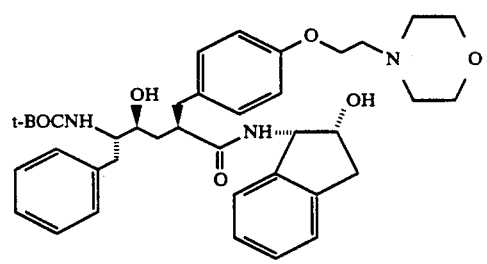

(2) incubating the compound of step (1) with Streptomyces culture #S-26-487 at temperatures ranging from about 20° C. to about 42° C. and at a pH in the range of from about 5.5 to 8.0 under aerobic conditions to prepare compound 1; and
(3) isolating the compound produced by step (2).

* * * * *